United States Patent [19]
Khandwala et al.

[11] Patent Number: 5,827,898
[45] Date of Patent: Oct. 27, 1998

[54] USE OF BISPHENOLIC COMPOUNDS TO TREAT TYPE II DIABETES

[75] Inventors: Atul S. Khandwala, San Carlos; Jian Luo, Brisbane, both of Calif.

[73] Assignee: Shaman Pharmaceuticals, Inc., South San Francisco, Calif.

[21] Appl. No.: 726,591

[22] Filed: Oct. 7, 1996

[51] Int. Cl.$^6$ ............................................. A61K 31/05
[52] U.S. Cl. .......................................... 514/734; 514/866
[58] Field of Search ..................................... 514/734, 866

[56] References Cited

U.S. PATENT DOCUMENTS

| | | | |
|---|---|---|---|
| 2,373,192 | 4/1945 | Lauer | 99/163 |
| 2,528,355 | 10/1950 | Fletcher et al. | 260/448.2 |
| 2,644,822 | 4/1953 | Pearl | 260/340.9 |
| 2,644,823 | 4/1953 | Kauck et al. | 260/345.1 |
| 2,734,088 | 2/1956 | Knowles et al. | 260/619 |
| 3,529,066 | 9/1970 | Barnhart | 424/346 |
| 3,934,034 | 1/1976 | Manning | 424/346 |
| 4,562,298 | 12/1985 | Parkhurst et al. | 568/644 |
| 4,695,590 | 9/1987 | Lippman | 514/724 |
| 4,708,964 | 11/1987 | Allen | 514/533 |
| 4,774,229 | 9/1988 | Jordan | 514/25 |
| 4,880,637 | 11/1989 | Jordan | 424/641 |
| 4,954,659 | 9/1990 | Parkhurst et al. | 568/651 |
| 5,008,294 | 4/1991 | Jordan et al. | 514/731 |
| 5,409,690 | 4/1995 | Howell et al. | 424/10 |
| 5,559,105 | 9/1996 | Bryan et al. | 514/63 |

FOREIGN PATENT DOCUMENTS

| | | |
|---|---|---|
| 3866M | 1/1966 | France . |
| 1046380 | 5/1965 | United Kingdom . |
| 1427441 | 3/1976 | United Kingdom . |
| 1361856 | 7/1994 | United Kingdom . |
| WO 88/03805 | 6/1988 | WIPO . |
| WO 92/20642 | 11/1992 | WIPO . |
| WO 94/02474 | 2/1993 | WIPO . |
| WO 93/14751 | 8/1993 | WIPO . |

OTHER PUBLICATIONS

Takahashi et al., 1990, "Elevated Plasma Endothelin in Patients with Diabetes Mellitus", Diabetologia 33:306–310.
Band et al., 1994, "Effects of inhibitors of lipoxygenase and cyclo–oxygenase enzymes on insulin secretion from Islets of Langerhans", Pharmacol. Comm. 4:285–294.
Bandoni et al., 1971, "Survey of Argentine medicinal plants. I. Folklore and phytochemical screening", Lloydia 35:69–77.
Brinker, 1993/94, "*Larrea tridentata* (D.C.) Coville (Chaparral or Creosote Bush)", Brit. J. Phytother. 3:10–29.
Christopher, 1976, *School of Natural Healing* (Christopher Publication, Provo, Utah).
Clapp, 1852, "Report on medical botany", Transactions of the American Medical Association V:750–751.
Dimayuga et al., 1986, "Traditional medicine of Baja California Sur (Mexico) I.", J. Ethnopharm. 17:183–193.
Dimayuga et al., 1987, "Traditional medicine of Baja California Sur (Mexico) II.", J. Ethnopharm. 20:209–222.
Guo et al., 1994, "Hypoglycemic and antiplatelet constituents of *Taxus mairei*", Chinese Pharm. J. 46:175–183.
Haworth et al., 1934, "The constituents of guaiacum resin. Part II. Synthesis of dl–guaiaretic acid dimethyl ether", J. Chem. Soc. pp. 1423–1429.
Hrdlicka, 1908, "Physiological and medical observations", *Bureau of American Ethnology* pp. 242, 244–245.
Ide and Buck, 1948, "The synthesis of benzoins", Org. React. 4:269–304.
Kellet et al., 1993, "Effect of nordihydroguaiaretic acid on glucose absorption, metabolism and (Na$^+$+K$^+$)—ATPase activity in rat jejunum", Biochem. Pharm. 45:1932–1935.
Kimura et al., 1994, "Diabetes mellitus–induced enhancement of prostaglandin $F_{2\alpha}$–responses is inhibited by lipoxygenase–but not cyclooxygenase–inhibitors in mesenteric veins and arteries of mouse and rat", Jpn. J. Pharmacol. 64:65–70.
Lieberman et al., 1947, "A synthesis of nordihydroguaiaretic acid", J. Am. Chem. Soc. 69:1540–1541.
Metz et al., 1983, "A role for the lipoxygenase pathway of arachidonic acid metabolism in glucose–and glucagon–induced insulin secretion", Life Sciences 32:903–910.
Metz et al., 1982, "Lipoxygenation of arachidonic acid: a pivotal step in stimulus–secretion coupling in the pancreatic beta cell", Endocrinology 111:2141–2143.

(List continued on next page.)

*Primary Examiner*—Kimberly Jordan
*Attorney, Agent, or Firm*—Pennie & Edmonds LLP

[57] ABSTRACT

This invention is directed to methods for treatment of non-insulin-dependent diabetes mellitus, for reducing blood glucose levels, or hyperglycemia. The methods entail administering to a mammal in need of such treatment a therapeutically effective amount of a composition whose active ingredient consists essentially of a compound of the following structure or a pharmaceutically acceptable salt thereof:

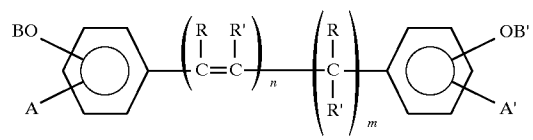

In the compound R and R' are independently H or a $C_1$–$C_{20}$ alkyl or $C_2$–$C_{20}$ alkenyl group which may be substituted or unsubstituted. Alternatively, R and R' are such that together a cycloalkyl or cycloalkenyl ring is formed. In the chain linking the two phenolic derivatives each of (C(R)=C(R')) or (C(R)(R')) are the same or different. A and A' are independently $C_2$–$C_{20}$ acylamino, $C_2$–$C_{20}$ acyloxy, $C_2$–$C_{20}$ alkanoyl, $C_2$–$C_{20}$ alkoxycarbonyl, $C_1$–$C_{20}$ alkoxyl, $C_1$–$C_{20}$ alkyl amino, $C_2$–$C_{20}$ alkyl carboxyl, amino, $C_2$–$C_{20}$ carbalkoxyl, carboxyl, cyano, halo, hydroxy. B and B' are independently H, $C_2$–$C_{20}$ alkanoyl, $C_3$–$C_{20}$ alkenoyl, $C_2$–$C_{20}$ alkenyl, $C_2$–$C_{20}$ alkoxycarbonyl, $C_1$–$C_{20}$ alkyl, aroyl, aralkanoyl, $C_2$–$C_{20}$ carbamoyl, or phosphate. The invention is also directed to methods of treatment using a bisphenolic compound in conjunction with another hypoglycemic or hypolipidemic agent.

3 Claims, 6 Drawing Sheets

OTHER PUBLICATIONS

North, 1908, "The native tribes of lower California", American Anthropologist 10:236–250.

Olsen, et al., 1991, A double–blind, vehicle–controlled study evaluating masoprocol cream in the treatment of actinic keratoses on the head and neck, J. Amer. Acad. Derm. 24:738–743.

Perez and Anesini, 1994, "Inhibition of *Pseudomonas aeruginosa* by Argentinean medical plants", Fitoterapia 65:169–172.

Perry et al., 1972, "Synthesis of lignans. I. Nordihydroguaiaretic acid", J. Orc. Chem. 37:4371–4376.

Robertson, 1984, "Arachidonic acid metabolism, the endocrine pancreas, and diabetes mellitus", Pharmac. Ther. 24:91–106.

Schroeter et al., 1918, "Uber die konstitution der Guajacharz–subztanzen", Ber. 51:1587.

Turk et al., 1985, "Arachidonic acid metabolism in isolated pancreatic islets. III. Effects of exogenous lipoxygenase products and inhibitors on insulin secretion", Biochem. Biophys. Acta. 834:23–26.

Vogel, 1970, *American Indian Medicine* (University of Oklahoma Press, Norman, Oklahoma).

Waller and Gisvold, 1945, "A phytochemical investigation of *Larrea divaricata* cav.", J. Amer. Pharm. Ass. Sci. 34:78–81.

Wilkinson and Orenberg, 1987, "Effects of nordihydroguaiaretic acid, phloretin, and phloridzin on the activity of adenylate cyclas, lipoxygenase and hexose transport, and growth of cultured keratinocytes", Int. J. Derm. 26:660–666.

Wilson et al., 1989, "Effect of nordihydroguaiaretic acid on cultured rat and human glioma cell proliferation", J. Nerosurg. 71:551–557.

Winkelman, 1989, "Ethnobotanical treatments of diabetes in Baja California Norte", Medical Anthropol. 11:255–268.

Winkelman, 1986, "Frequently used medicinal plants in Baja California Norte", J. Ethnopharm. 18:109–131.

Yamamoto et al., 1983, "Modulation of insulin secretion by lipoxygenase products of arachidonic acid", J. Biol. Chem. 12149–12152.

Zamora et al., 1992, "A comparison of the cytotoxicity of nordihydroguaiaretic acid and its derivatives", J. Tenn. Acad. Sci. 67:77–80.

USE OF BISPHENOLIC COMPOUNDS TO TREAT TYPE II DIABETES

TABLE OF CONTENTS
1. FIELD OF THE INVENTION
2. BACKGROUND OF THE INVENTION
   2.1 ETHNOBOTANY OF LARREA TRIDENTATA
   2.2 CHEMISTRY AND BIOLOGY OF NDGA AND OTHER BISPHENOLIC COMPOUNDS
3. SUMMARY OF THE INVENTION
4. DESCRIPTION OF THE FIGURES
5. DETAILED DESCRIPTION OF THE INVENTION
6. EXAMPLE: HYPOGLYCEMIC ACTIVITY OF NDGA
   6.1 HYPOGLYCEMIC ACTIVITY IN A db/db MODEL
   6.2 HYPOGLYCEMIC ACTIVITY IN ob/ob MODEL
   6.3 BENEFICIAL -EFFECT ON GLUCOSE DISPOSAL
   6.4 STIMULATION OF GLUCOSE TRANSPORT

1. FIELD OF THE INVENTION

This invention relates to a novel method of treating Type II diabetes, a method for lowering the blood glucose levels and a method for treatment of hypoglycemia and hypoglycemia associated abnormalities in mammals. The method utilizes the bisphenolic compounds described herein including nordihydroguiaretic acid (NDGA), NDGA derivatives and NDGA analogs.

2. BACKGROUND OF THE INVENTION

2.1 ETHNOBOTANY OF LARREA TRIDENTATA

Larrea spp. (Zigophyllaceae) are used as botanical medicines in several parts of the New World. In the United States, *L. tridentata* reportedly was used traditionally as a tonic and as a treatment for numerous ailments, including sores, wounds, rheumatism, and bowel cramps (Waller, C. W. and Gisvold, O., 1945, "A phytochemical investigation of Larrea divaricata cav.," *J. Amer. Pharm. Ass. Sci.*, 34:78–81). This plant still has widespread medicinal use today among several groups of traditional peoples in the Southwest United States and in Mexico (Brinker, F., 1993/94, *"Larrea tridentata* (D.C.) Coville (Chaparral or Creosote Bush)," *Brit. J. Phytother.* 3(1):10–29.; Dimayuga, R. E.; Murillo, R. F.; Pantoja, M. L., 1987, "Traditional medicine of Baja California Sur (Mexico) II," *J. Ethnopharm.*, 20:209–222; Winkelman, M., 1986, "Frequently used medicinal plants in Baja California Norte," *J. Ethnopharm.* 18:109–131). Oral decoctions and hot water extracts of dried branches or dried leaf or dried root of Larrea tridentata are used in Baja California to treat diabetes (Dimayuga, et al., 1987, supra; Winkelman, 1989, "Ethnobotanical Treatments of Diabetes in Baja California Norte," *Medicinal Anthropology,* 11:255–268).

Dried leaf decoctions of Larrea tridentata are also taken as a therapy for kidney problems and urinary tract infections, rheumatism and arthritis, wounds and skin injuries, and paralysis (Winkelman, 1986, supra). Today in Baja Calif. Sur, some of the local people reportedly utilize *Larrea tridentata* in treatments for rheumatism, stomach ache, and ulcers. Several elder local informants of Baja California Sur recalled that *Larrea tridentata* was employed to treat foot infections, kidney pain, diabetes, high blood pressure, and headache (Dimayuga, et al., 1987, supra). These informants claimed that their knowledge of medicinal plants was passed down to them by their forebears, the Pericues. During the time of the Spanish incursion in Baja Calif. the Pericues were one of several indigenous tribes inhabiting the area that now constitutes the southernmost part of Baja Calif. (Dimayuga, R. E. and Agundez, J., 1986, "Traditional medicine of Baja Calif. Sur (Mexico) II," *J. Ethnopharm.* 17:183–193; North, A. W., 1908, "The native tribes of lower California," *American Anthropologist.* 10:236–250 (Reprint, 1962; New York: Kraus Reprint Corp.)).

In Argentina, a dried leaf decoction of L. divaricata (jarilla in vernacular) is used externally for the treatment of inflammation (Bandoni, A. L.; Mendiondo, M. E.; Rondina, R.V.D.; Coussio, J. D., 1972, "Survey of Argentine medicinal plants. I. Folklore and phytochemical screening," Lloydia, 35(1):69–77) and orally as a therapy for urinary tract infections (Perez, C. and Anesini, C., 1994, "Inhibition of *pseudomonas aeruginosa* by Argentinean medicinal plants," Fitoterapia, 65(2):169–172). In the United States, oral hot water extracts of L. divaricata are administered in the treatment of arthritis and inflammation (Christopher, J. R., 1976, *School of Natural Healing,* Provo, Utah: Christopher Publ.).

In the mid-nineteenth century, a surgeon documented the medicinal use of *Larrea tridentata* by Native Americans in New Mexico (Vogel, V. J., 1970, *American Indian Medicine,* Norman and London: Univ Oklahoma Press; Clapp, A., 1852, "Report on medical botany," *Transactions of the American Medical Association,* Vol. V:750–751). Indigenous Amerindian populations throughout the Southwest, certain areas of the Southeast, and possibly Mexico historically utilized this species in traditional remedies for numerous ailments. Among Southwest tribes, the Pima and Maricopa reportedly used fresh twigs and branches of *Larrea tridentata* in therapies for rheumatic and body pain (Vogel, 1970; Hrdlicka, A., 1908, "Physiological and medical observations," *Bureau of American Ethnology.* p. 242, 244–245). Another Southwest Indian people, the Papago, treated contusions with topical solutions of a hot decoction of boiled leaves of *Larrea tridentata* mixed with salt (Vogel, 1970, supra; Hrdlicka, 1908, supra).

2.2 CHEMISTRY AND BIOLOGY OF NDGA AND OTHER BISPHENOLIC COMPOUNDS

Nordihydroguiaretic Acid (NDGA) is also known as (R*, S*)-4,4'-(2,3-dimethyl-1,4-butanediol)bis[1,2-benzenediol]; meso-4,4'-(2,3'-dimethyletramethylene dipyrocatechol; 2,3-bis(3,4'-dihydroxybenzyl)butane; β,γ-dimethyl-α,δ-bis(3,4-dihydroxyphenylbutane); masoprocol; CHX-100; and ACTINEX®. The structure is shown below.

It occurs naturally as the meso-form in the leaves and small stems of the creosote bush, *Larrea divaricata,* Zigophyllaceae (Covillea tridentata). The isolation was first reported by Walter et al. in 1945 (Walter, 1L945, supra). The preparation from guaiaretic acid dimethyl ether was reported by Schroeter and Haworth (G. Schroeter et al., 1918, Ber. 51:1587; R. D. Haworth et al., 1934, *J. Chem. Soc.,* pp. 1423). The synthesis of NDGA was reported by Lieberman (Lieberman et al., 1947, *J. Am. Chem. Soc.,* 69:1540) and the stereochemistry of the naturally occurring form was assigned by Perry (Perry et al., 1972, *J. Org. Chem.,* 37:4371).

The use as of NDGA as an antioxidant was described by Lauer in U.S. Pat. No. 2,373,192. NDGA has been used as an antioxidant to inhibit rancidity of fats and as a stabilizer of pharmaceutical preparations.

Other workers have noted that NDGA has an antiproliferative effect on cultured keratinocytes and on cultured glioma cells (Wilkinson and Orenberg, 1987, *Int. J. Dermatol.*, 26:660; D. E. Wilson et al., 1989, *J. Neurosurg.*, 71:551, respectively). Olsen et al. reported a clinical trial for actinic keratoses (Olsen et al., 1991, *J. Am. Acad. Dermatol.*, 24:738). The meso and other isomeric forms have been claimed to be useful for topical treatment of tumors and other keratoses of the skin (U.S. Pat. No. 5,008,294), for reversing multidrug resistant diseases in cancer cells (U.S. Pat. No. 5,409,690), to retard aging (U.S. Pat. No. 4,695,590), and to be an inhibitor of the lipoxygenase pathway of arachidonic acid and useful for the treatment of psoriasis (U.S. Pat. No. 4,708,964). NDGA has been marketed for the topical treatment of actinic keratoses under the trademark ACTINEX® or the generic name masoprocol.

NDGA and certain analogs have also been reported to reduce cholesterol and triglyceride levels, specifically hyperlipidemia (U.S. Pat. No. 3,934,034) and to be a metabolic stimulant (French patent FR 3866M). Others have reported that 2,2'-alkylidene bisdialkyl phenols lower serum cholesterol. Vanadium and niobium complexes of a large variety of catechol derivatives including NDGA were claimed to be hypocholesterolemic, hypolipidemic and to be useful for the treatment of diabetes (PCT Publication No. WO 93/14751). However, these phenolic substances were present only as carriers for the metal ions and were not reported or claimed to possess activity in their own right.

NDGA is known as a lipoxygenase inhibitor. There is considerable confusion in the literature about the effects of arachidonic acid metabolites and of cyclooxygenase and lipoxygenase inhibitors on insulin secretion (A. M. Band, et al., 1994, *Pharmacology Communications*, p. 285). Numerous publications report that NDGA and numerous other lipoxygenase inhibitors inhibit the release of glucose induced insulin secretion (see for example S. Yamamoto, et al., 1983, *J. Biological Chem.*, p. 12149, and A. M. Band, et al. 1994). However, there are no reports showing plasma glucose lowering.

Surprisingly it has now been discovered that the bisphenolic compounds, including nordihydroguiaretic acid, NDGA, its stereoisomers, analogs and derivatives as illustrated below, are effective in lowering blood sugar and in the treatment of diabetes, especially Type II diabetes.

Citation or identification of any reference in Section 2 of this application shall not be construed as an admission of prior art to the present invention.

3. SUMMARY OF THE INVENTION

This invention is directed to methods for treatment of non-insulin-dependent diabetes mellitus, for reducing blood glucose levels, or for treatment of hypoglycemia. The methods comprise administering to a mammal in need of such treatment a therapeutically effective amount of a composition whose active ingredient consists essentially of a compound of the following structure (or a geometric or optical isomer) or a pharmaceutically acceptable salt thereof:

In the compound(s) R and R' are independently H or a $C_1$–$C_{20}$ alkyl or a $C_2$–$C_{20}$ alkenyl group which may be branched or unbranched. In a preferred embodiment R and R' are independently H or a $C_1$–$C_{10}$ alkyl, more preferably a $C_1$–$C_6$ alkyl, or a $C_2$–$C_{10}$ alkenyl, more preferably a $C_2$–$C_8$, alkenyl, which may be substituted or not substituted. Alternatively, R and R' are such that together a cycloalkyl or cycloalkenyl ring is formed. Each of (C(R)=C(R')) and/or (C(R)(R')) may be the same or different. A and A' are independently a $C_2$–$C_{20}$ alkanoyl, preferably $C_2$–$C_{10}$ alkanoyl, more preferably $C_2$–$C_6$ alkanoyl; $C_2$–$C_{20}$ acylamino, preferably $C_2$–$C_{10}$ acylamino, more preferably $C_2$–$C_6$ acylamino; $C_2$–$C_{20}$ acyloxy, preferably $C_2$–$C_{10}$ acyloxy, more preferably $C_2$–$C_6$ acyloxy; $C_1$–$C_{20}$ alkoxy, preferably $C_1$–$C_{10}$ alkoxy, more preferably $C_1C_6$ alkoxy; $C_2$–$C_{20}$ alkoxycarbonyl, preferably $C_2$–$C_{10}$ alkoxycarbonyl, more preferably $C_2$–$C_6$ alkoxycarbonyl; $C_1$–$C_{20}$ alkyl amino, preferably $C_1$–$C_{10}$ alkyl amino, more preferably $C_1$–$C_6$ alkyl amino; $C_2$–$C_{20}$ alkylcarboxyl, preferably $C_2$–$C_{10}$ alkylcarboxyl, more preferably $C_2$–$C_6$ alkylcarboxyl, amino, $C_2$–$C_{20}$ carbalkoxyl, preferably $C_2$–$C_{10}$ carbalkoxyl, more preferably $C_2$–$C_6$ carbalkoxyl, carboxyl, cyano, halo, or hydroxy. The substituents on the phenolic oxygen B and B' are independently H, $C_2$–$C_{20}$ alkanoyl, $C_3$–$C_{20}$ alkenoyl, $C_2$–$C_{20}$ alkenyl, $C_2$–$C_{20}$ alkoxycarbonyl, $C_1$–$C_{20}$ alkyl, aroyl, aralkanoyl, $C_2$–$C_{20}$ carbamoyl, or phosphate. In a preferred embodiment, B an B' are independently H, a $C_2$–$C_{10}$ alkanoyl, more preferably $C_2$–$C_6$ alkanoyl; a $C_3$–$C_{10}$ alkenoyl, more preferably $C_3$–$C_6$ alkenoyl; a $C_2$–$C_{10}$ alkenyl, more preferably $C_2$–$C_6$ alkenyl; a $C_2$–$C_{10}$ alkoxycarbonyl, more preferably $C_2$–$C_6$ alkoxycarbonyl; $C_1$–$C_{10}$ alkyl, more preferably a $C_1$–$C_6$ alkyl, a $C_2$–$C_{10}$ carbamoyl, more preferably a $C_2$–$C_6$ carbamoyl, or phosphate. When both A and A' are alkoxy, at least one of B and B' is H.

In the compounds utilized in this method, n and m are independently equal to 0 to 6. The invention is also directed to the use of geometric and optical isomers of compounds having the structure above.

In one embodiment of the method in the compounds, B and B' are hydrogen and A and A' are independently hydroxyl or $C_2$–$C_{20}$ acyloxy. Alternatively, B and B' are hydrogen and A and A' are hydroxyl.

In another embodiment of the method in the compounds, n is 0 and m is 2 to 4 and each of R and R' is independently hydrogen or $C_1$–$C_{20}$ alkyl, or a $C_1$–$C_{10}$ alkyl or a $C_1$–$C_6$ alkyl. In a preferred embodiment of the method in the compounds, B and B' are hydrogen; A and A' are independently hydroxyl or $C_1$–$C_{20}$ acyloxy; n is 0; m is 2 to 4; and R and R' are independently hydrogen or $C_1$–$C_{20}$ alkyl or a $C_1$–$C_{10}$ alkyl, or a $C_1$–$C_6$ alkyl.

In the methods described herein, the compound utilized may be meso, d-, l- or dl- 4,4'-(2,3-dimethyl-1,4-butanediol) bis[1,2-benzenediol]. In a particular embodiment, it is nordihydroguiaretic acid.

The invention also encompasses combination therapies. For example, this invention provides methods for treating non-insulin-dependent diabetes mellitus, treating hypoglycemia, or reducing blood glucose level, which comprise administering to a mammal in need of such treatment a therapeutically effective amount of a composition whose active ingredients consist essentially of a (i) hypoglycemic or hypolipidemic agent selected from the group consisting of a sulfonylurea, a biguanide, a thiazolidine, a beta-3- adrenoceptor antagonist, an alpha-glycosidase inhibitor and insulin and (ii) a compound of the following structure (or a geometric or optical isomer) or a pharmaceutically acceptable salt thereof:

where A, A', B, B', R, R', m, n, (C(R)=C(R')) and (C(R)(R')) are as defined above.

According to another example, this invention provides methods for treating non-insulin-dependent diabetes mellitus, treating hypoglycemia, or reducing blood glucose level, which comprise administering to a mammal in need of such treatment a therapeutically effective amount of: (i) a composition whose active ingredient consists essentially of a compound of the following structure (or a geometric or optical isomer) or a pharmaceutically acceptable salt thereof:

wherein A, A', B, B', R, R', m, n, (C(R)=C(R')) and (C(R)(R')) are as defined above, in conjunction with (ii) a composition comprising a hypoglycemic or hypolipidemic agent selected from the group consisting of a sulfonylurea, a biguanide, a thiazolidine, a beta-3- adrenoceptor antagonist, an alpha-glycosidase inhibitor and insulin. According to this mode of the invention, the two compositions can be administered at the same time or one of the compositions can be administered shortly before the other.

Suitable pharmaceutically acceptable salts according to the present invention include but are not limited to hydrochloride, hydrobromide, phosphate, sulfate, acetate, succinate, ascorbate, tartrate, gluconate, benzoate, malate, and fumarate.

The bisphenolic compound is used in these methods at a dose of about 1 to 1000 mg/kg per day; preferably at a dose of about 1 to 350 mg/kg per day.

4. DESCRIPTION OF THE FIGURES

The present invention may be understood more fully by reference to the following detailed description examples of specific embodiments of the invention and the appended figures of which.

5. DETAILED DESCRIPTION OF THE INVENTION

This invention is directed to methods for treatment of non-insulin-dependent diabetes mellitus, for reducing blood glucose levels, and for treatment of hypoglycemia. The methods comprise administering to a mammal in need of such treatment a therapeutically effective amount of a composition whose active ingredient consists essentially of a compound of the following structure (or a geometric or optical isomer) thereof, or a pharmaceutically acceptable salt thereof:

In the compound(s) R and R' are independently H or a $C_1$–$C_{20}$ alkyl or $C_2$–$C_{20}$ alkenyl group which may be branched or unbranched. In a preferred embodiment R and R' are independently H or a $C_1$–$C_{10}$ alkyl, more preferably a $C_1$–$C_6$ alkyl, or a $C_2$–$C_{10}$ alkenyl, more preferably a $C_2$–$C_8$ alkenyl, which may be substituted or not substituted. Alternatively, R and R' are such that together a cycloalkyl or cycloalkenyl ring is formed. Each of (C(R)=C(R')) and/or (C(R)(R')) may be the same or different. A and A' are independently $C_2$–$C_{20}$ alkanoyl, preferably $C_2$–$C_{10}$ alkanoyl, more preferably $C_2$–$C_6$ alkanoyl; $C_2$–$C_{20}$ acylamino, preferably $C_2$–$C_{10}$ acylamino, more preferably $C_2$–$C_6$ acylamino; $C_2$–$C_{20}$ acyloxy, preferably $C_2$–$C_{10}$ acyloxy, more preferably $C_2$–$C_6$ acyloxy; $C_1$–$C_{20}$ alkoxy, preferably $C_1$–$C_{10}$ alkoxy, more preferably $C_1$–$C_6$ alkoxy; $C_2$–$C_{20}$ alkoxycarbonyl, preferably $C_2$–$C_{10}$ alkoxycarbonyl, more preferably $C_2$–$C_6$ alkoxycarbonyl; $C_1$–$C_{20}$ alkyl amino, preferably $C_1$–$C_{10}$ alkyl amino, more preferably $C_1$–$C_6$ alkyl amino; $C_2$–$C_{20}$ alkylcarboxyl, preferably $C_2$–$C_{10}$ alkylcarboxyl, more preferably $C_2$–$C_6$ alkylcarboxyl, amino, $C_2$–$C_{20}$ carbalkoxyl, preferably $C_2$–$C_{10}$ carbalkoxyl, more preferably $C_2$–$C_6$ carbalkoxyl, carboxyl, cyano, halo, or hydroxy. The substituents on the phenolic oxygen B and B' are independently H, $C_2$–$C_{20}$ alkanoyl, $C_3$–$C_{20}$ alkenoyl, $C_2$–$C_{20}$ alkenyl, $C_2$–$C_{20}$ alkoxycarbonyl, $C_1$–$C_{20}$ alkyl, aroyl, aralkanoyl, $C_2$–$C_{20}$ carbamoyl, or phosphate. In a preferred embodiment, B an B' are independently H, a $C_2$–$C_{10}$ alkanoyl, more preferably $C_2$–$C_6$ alkanoyl; a $C_3$–$C_{10}$ alkenoyl, more preferably $C_3$–$C_6$ alkenoyl; a $C_2$–$C_{10}$ alkenyl, more preferably $C_2$–$C_6$ alkenyl; a $C_2$–$C_{10}$ alkoxycarbonyl, more preferably $C_2$–$C_6$ alkoxycarbonyl; $C_1$–$C_{10}$ alkyl, more preferably a $C_1$–$C_6$ alkyl, a $C_2$–$C_{10}$ carbamoyl, more preferably a $C_2$–$C_6$ carbamoyl, or phosphate. When both A and A' are alkoxy, at least one of B and B' is H.

In the compounds utilized in this method, n and m are independently equal to 0 to 6. The invention is also directed to the use of geometric and optical isomers of compounds having the structure above.

In one embodiment of the method in the compounds, B and B' are hydrogen and A and A' are independently hydroxyl or $C_2$–$C_{20}$ acyloxy. Alternatively, B and B' are hydrogen and A and A' are hydroxyl.

In another embodiment of the method in the compounds, n is 0 and m is 2 to 4 and each of R and R' is independently hydrogen or $C_1$–$C_{20}$ alkyl, or a $C_1$–$C_{10}$ alkyl or a $C_1$–$C_6$ alkyl. In a preferred embodiment of the method in the compounds, B and B' are hydrogen; A and A' are independently hydroxyl or $C_{1-20}$ acyloxy; n is 0; m is 2 to 4; and R and R' are independently hydrogen or $C_1$–$C_{20}$ alkyl or a $C_1$–$C_{10}$ alkyl, or a $C_1$–$C_6$ alkyl.

In the methods described herein, the compound utilized may be meso, d-, l- or dl- 4,4'-(2,3-dimethyl-1,4-butanediol) bis[1,2-benzenediol]. In a particular embodiment, it is nordihydroguiaretic acid.

When R and R' are such that they form a ring, the ring will be from 3 to 10 member ring. Typically, R and R' will be such that a 5 or 6 member ring is formed.

As used herein, aroyl includes the acyl derivatives of benzene, naphthalene, pyridine, thiophene or quinoline, optionally substituted with alkyl, halo, hydroxy, alkoxy, amino, nitro, carboxyl or carbalkoxyl groups, and aralkanoyl refers to alkanoyl derivatives substituted by phenyl, naphthyl, pyridyl, thienyl, or quinolinyl rings optionally substituted with alkyl, halo, hydroxy, alkoxy, amino, nitro, carboxyl or carbalkoxyl groups.

As used herein, geometric and optical isomers includes cis and trans isomers about double bonds, cis and trans isomers of cyclic compounds, diastereomers, enantiomers and compounds with one or more chiral centers and racemic mixtures thereof.

Alternatively, the compound may have the structure below, wherein A, A', B, B', R, R'and n are as defined as above and each m may the same or different and may be 0 or 1.

Suitable pharmaceutically acceptable salts according to the present invention include but are not limited to hydrochloride, hydrobromide, phosphate, sulfate, acetate, succinate, ascorbate, tartrate, gluconate, benzoate, malate, and fumarate.

The invention also encompasses combination therapies. For example, this invention provides methods for treating non-insulin-dependent diabetes mellitus, for treating hypoglycemia, or for reducing blood glucose levels, which comprise administering to a mammal in need of such treatment a therapeutically effective amount of a composition whose active ingredient consists essentially of a (i) hypoglycemic or hypolipidemic agent selected from the group consisting of a sulfonylurea, a biguanide, a thiazolidine, a beta-3- adrenoceptor antagonist, an alphaglycosidase inhibitor and insulin and (ii) a compound of the following structure (or a geometric or optical isomer) or a pharmaceutically acceptable salt thereof:

where A, A', B, B', R, R', m, n, (C(R)=C(R')) and (C(R)(R')) are as defined above.

According to another example, this invention provides methods for treating non-insulin-dependent diabetes mellitus, treating hypoglycemia, or reducing blood glucose level, which comprise administering to a mammal in need of such treatment a therapeutically effective amount of: (i) a composition whose active ingredient consists essentially of a compound of the following structure (or a geometric or optical isomer) or a pharmaceutically acceptable salt thereof:

Specific analogs which are envisaged to be useful according to the methods of the invention include, but are not limited to the following:

| A | BO— | A' | B'O— | $-(\overset{R\ R'}{\underset{}{C=C}})_N-$ | $-(\overset{R}{\underset{R'}{C}})_M-$ |
|---|---|---|---|---|---|
| 3-HO | 4-HO | 3-HO | 4-HO | —CH=CH— | — |
| 3-AcO | 4-AcO | 3-AcO | 4-AcO | — | —$CH_2CH(CH_3)CH(CH_2CH_3)$— |
| 2-HO | 3-HO | 2-HO | 3-HO | —$C(CH_3)$=CH— | $C(CH_3)_2$— |
| 3-$CH_3O$ | 4-HO | 3-$CH_3O$ | 4-HO | — | —$(CH_2)$— |
| 3-$CH_3OCO$ | 5-$CH_3OCO$ | 3-$CH_3OCO$ | 5-$CH_3OCO$ | — | —$CH_2CH(CH_3)CH_2CH_2$— | where A, A', B, B', R, R', m, n, (C(R)=C(R')) and (C(R)(R')) are as defined above. The compound may be used in conjunction with (ii) a composition comprising hypoglycemic or hypolipidemic agent selected from the group consisting of a sulfonylurea, a biguanide, a thiazolidine, a beta-3-adrenoceptor antagonist, an alpha-glycosidase inhibitor and insulin. According to this mode of the invention, the two compositions can be administered at the same time or one of the compositions can be administered shortly before the other. The bisphenolic compound is used in these methods at a dose of about 1 to 1000 mg/kg per day; preferably at a dose of about 1 to 350 mg/kg per day.

Suitable biguanides include metformin and buformin; suitable sulfonylureas include acetohexamide, chlorpropamide, tolazamide, tolbutamide, glyburide, glypizide and glyclazide; suitable thiazolidinediones include troglitazone; α-glycosidase inhibitors include acarbose and miglatol; suitable $\beta_3$-adrenoceptor agonists include CL-316, 243, etc.

The bisphenolic compounds utilized in the methods of this invention may be synthesized by means well known to those skilled in the art. For example substituted 2,2'-alkylidene bisphenols may be made by reaction with p-formaldehyde, acetaldehyde or other aldehyde in the presence of an acid catalyst as described in U.S. Pat. Nos. 3,529,066, 2,528,355, 2,570,402 and 2,734,088.

Compounds with a two carbon chain between the aromatic rings (stilbene derivatives) may be made by a benzoin condensation and subsequent reduction (see Ide and Buck, 1948, *Org. React.*, 4:269–304). Alternatively, such compounds and those with longer chains may be made by a McMurry coupling of appropriate carbonyl starting materials (McMurry, 1989, *Chem. Rev.*, 89:1513–1524). Compounds with a longer carbon chain between the aromatic rings may be prepared as described in British Publication GB 1046380 or PCT Publication No. WO88/03805. Additional synthetic methods may be found in U.S. Pat. Nos. 4,954,298 (1990), 4,562,298 (1985), and 2,644,182 (1953). Also, see Lieberman, 1947, *J. Am. Chem. Soc.*, 1540.

The phenolic esters are readily prepared using standard methods such as reaction of the phenol with an acid chloride in the presence of a base. The phenolic ethers are easily prepared using standard methods of synthesis such as reaction of the phenol with an alkyl halide in the presence of a base.

The compounds utilized in the methods described herein are particularly suited to control hypoglycemia in patients whose blood glucose cannot be controlled by diet alone. As described above, these compounds may be used alone or in combination with other known antidiabetic or hypolipidemic agents. The compounds including NDGA, derivatives and analogs, or pharmaceutically acceptable salts thereof can be administered via the parenteral, oral or rectal routes or by inhalation. The compounds can be administered by injection including, but not limited to intravenously, intraperitoneally, subcutaneously, intramuscularly, etc. They are advantageously effective when administered orally. In humans, the compounds can be administered orally in the form of tablets, capsules, sustained release tablets or capsules, or in other generally accepted oral formulations, including but not limited to liquid dosage forms.

In a further embodiment, this invention comprises the use of a bisphenolic compound when administered at a dose of 1 to 1,000 mg per kg per day. In still a further embodiment, the invention comprises the use of a bisphenolic compound at a dose of 1 to 350 mg/kg per day. Generally, the efficacious amount (1 to 350 mg/kg) of compound to be utilized is an amount which results in the composition's exhibiting a therapeutically effective hypoglycemic, antihypoglycemic or antidiabetic activity. In a pharmacodynamic study in db/db mice, the present inventors have shown that a single dose of a bisphenolic compound, i.e., NDGA, administered orally, reduced blood glucose level as early as 1.5 h after administration; the reduced blood glucose level was maintained for at least an additional 6.5 h.

As described above, the bisphenolic compounds are advantageously used to treat diabetes. Additionally, the bisphenolic compounds can advantageously be used as hypoglycemic agents to reduce the blood glucose level in situations of acute stress such as experienced by animals or patients with hyperthermia, trauma, sepsis, and burns and undergoing general anesthesia. Hypoglycemia sometimes associated with severe head injury, cerebral thrombosis, encephalitis and heat stroke can also be therapeutically treated with these biologically active compounds. Additionally, the bisphenolic compounds are useful as hypoglycemic agents for rare congenital metabolic glycogen storage disease associated with hypoglycemia.

The compounds described herein or pharmaceutically acceptable salts thereof and compositions containing the compounds described herein, or pharmaceutically acceptable salts thereof can be used for research purposes, for example, to investigate the mechanism and activity of hypoglycemic agents.

The following examples are set forth to assist in understanding the invention and should not, of course, be construed as specifically limiting the invention described and claimed herein. Such variations of the inventions which would be within the purview of those in the art, including the substitution of all equivalents now known or later developed, including changes in formulation or minor changes in experimental design, are to be considered to fall within the scope of the invention as hereinafter claimed.

A number of references are cited herein, the entire disclosures of which are incorporated herein, in their entirety, by reference.

6. EXAMPLE: HYPOGLYCEMIC ACTIVITY OF NDGA

The following experiments demonstrate that the compounds described herein, for example NDGA, produce a significant and consistent hypoglycemic effect on obese diabetic mice, i.e., an art recognized model of diabetes mellitus. Further demonstrated are NDGA's beneficial effects on glucose tolerance and the ability to stimulate glucose transport in adipocytes.

6.1 HYPOGLYCEMIC ACTIVITY IN A db/db MODEL

This experiment illustrates the effectiveness of NDGA in reducing plasma glucose levels in obese diabetic db/db mice, a model recognized by those skilled in the art as being a representative model of non-insulin-dependent diabetes mellitus (NIDDM).

Protocol

Genetically altered obese diabetic mice (designated C57BL/Ks-db/db) were purchased from The Jackson Laboratory (Bar Harbor, Me., USA), and served as experimental animals. Male animals between the ages of 8–9 weeks were employed in the studies described here. Animals were housed (4 mice/cage) under standard laboratory conditions at 22° C. and 50% relative humidity, and were maintained on a diet of Purina rodent chow and water ad libitum. Prior to treatment, blood was collected from the tail vein of each animal. Mice that had plasma glucose levels between 350 and 600 mg/dl were used. Each treatment group consisted of eight mice that were distributed so that the mean glucose levels were equivalent in each group at the start of the study. Diabetic mice designated C57BLIKS-db/db received, orally by gavage, daily for 2 days either vehicle, NDGA administered at 150 mg/kg bid (9:00 and 17:00), 250 and 350 mg/kg q.d., or metformin [250 mg (1510 mol)/kg q.d]. Compounds were delivered in a liquid vehicle containing 0.25% (w/v) carboxymethylcellulose, 1% (v/v) "TWEEN™" 60, and up to 10% (v/v) dimethyl sulfoxide (DMSO) in a volume of 10 ml/kg. Blood was sampled from the tail vein three hours post-dosing (3 and 27 hours), and analyzed for plasma glucose levels. Individual body weights and mean food consumption (each cage) were also measured after 24 h. was used as obtained.

Metformin (1, 1-dimethylbiguanide) was purchased from Sigma Chemical Co. (St. Louis, Mo., USA; catalog# D-5035). NDGA was purchased from Sigma Chemical Co. (St. Louis, Mo., USA; catalog# D-5023). Plasma glucose levels were determined calorimetrically using glucose oxidase (Sigma Chemical Co.; Sigma catalog# 315). Significant differences between groups (comparing drug-treated to vehicle-treated) were evaluated using analysis of variance and Fisher's post-hoc test.

Results

Figure 1:
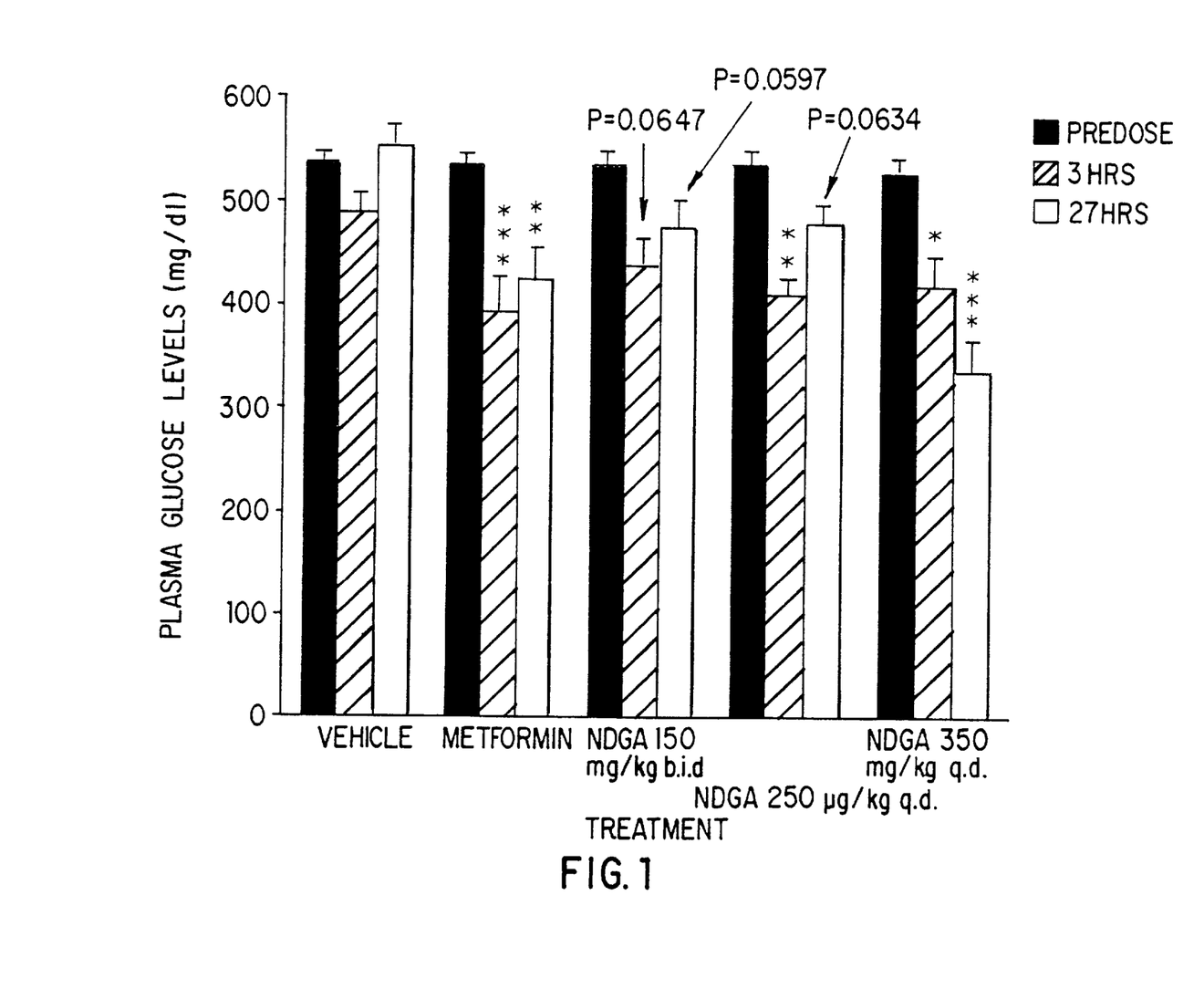
FIG. 1 is a histogram showing the plasma glucose levels of diabetic db/db mice treated with varying doses of NDGA. (*$P<0.05$, $P<0.01$, *$P<0.001$ (Anova, one factor) $N=8$).

As shown in FIG. 1 and below in Table 1, oral administration of the NDGA to diabetic C57BL/Ks-db/db mice once daily for 2 days at dosage levels of 250 and 350 mg/kg resulted in dose dependent reduction in plasma glucose. Statistically significant glucose reduction relative to vehicle (control) was observed after 3h at both dosage levels and 27h at 350 mg/kg. NDGA at 150 mg/kg twice daily also reduced plasma glucose levels. The change in body weight and overall food consumption values for mice treated with NDGA are shown in Table 2. No significant effects on the body weight and food consumption were observed with NDGA treatment up to 250 mg/kg q.d.

TABLE 1

Effects of NGDA on Blood Glucose in Diabetic db/db Mice

| Treatment | Dose (mg/kg) | Change in Glucose (mg/dL) 3 h | P Value | Change in Glucose (mg/dL) 27 h | P Value |
|---|---|---|---|---|---|
| Vehicle | — | −48.0 | NA | −16.5 | NA |
| Metformin | 250 qd | −140.9 | 0.0009 | −111.1 | 0.0013 |
| NDGA | 150 bid | −98.0 | 0.0647 | −58.7 | 0.0597 |
| NDGA | 250 qd | −124.9 | 0.0052 | −55.3 | 0.0634 |
| NDGA | 350 qd | −109.5 | 0.0147 | −190.8 | <0.0001 |

NA = non-applicable

TABLE 2

Effects of NGDA on Body Weight and Food Consumption in Diabetic db/db Mice

| Treatment | Dose (mg/kg) | Change in Body Weight (g) 24 h | Food Consumption (g/mouse) 0–24 h |
|---|---|---|---|
| Vehicle | — | 0.1 | 6.1 |
| Metformin | 250 qd | −0.3 | 5.1 |
| NDGA | 150 qd | −0.1 | 5.4 |
| NDGA | 250 qd | −0.0 | 4.7 |
| NDGA | 350 qd | −0.6 | 3.6 |

6.2 HYPOGLYCEMIC ACTIVITY IN ob/ob MODEL

This experiment illustrates the effectiveness of NDGA in reducing plasma glucose levels in obese diabetic ob/ob mice, a model recognized by those skilled in the art as being a representative model of non-insulin-dependent diabetes mellitus (NIDDM).

Protocol

Genetically altered obese diabetic mice (designated C57BL/6J ob/ob) were purchased from The Jackson Laboratory (Bar Harbor, Me., USA), and served as experimental animals. Male animals between the ages of 8–9 weeks were employed in the studies described here. Animals' housing condition was the same as described above in Section 6.1. Mice that had plasma glucose levels between 300 and 500 mg/dl were used. Each treatment group consisted of eight mice that were distributed so that the mean glucose levels were equivalent in each group at the start of the study. Mice received, orally by gavage daily for 3 days, either vehicle, NGDA administered at 250 mg/kg, or metformin (250 mg/kg). Compounds were delivered in a liquid vehicle containing 0.25% (w/v) carboxymethylcellulose, 1% (v/v) TWEEN™ 60, and up to 10% (v/v) dimethyl sulfoxide (DMSO) in a volume of 10 ml/kg. Blood was sampled from the tail vein three hours post-dosing (3, 27 and 51 hours), and analyzed for plasma glucose levels. Individual body weights and mean food consumption (each cage) were also measured every 24 h.

Results

Figure 2:
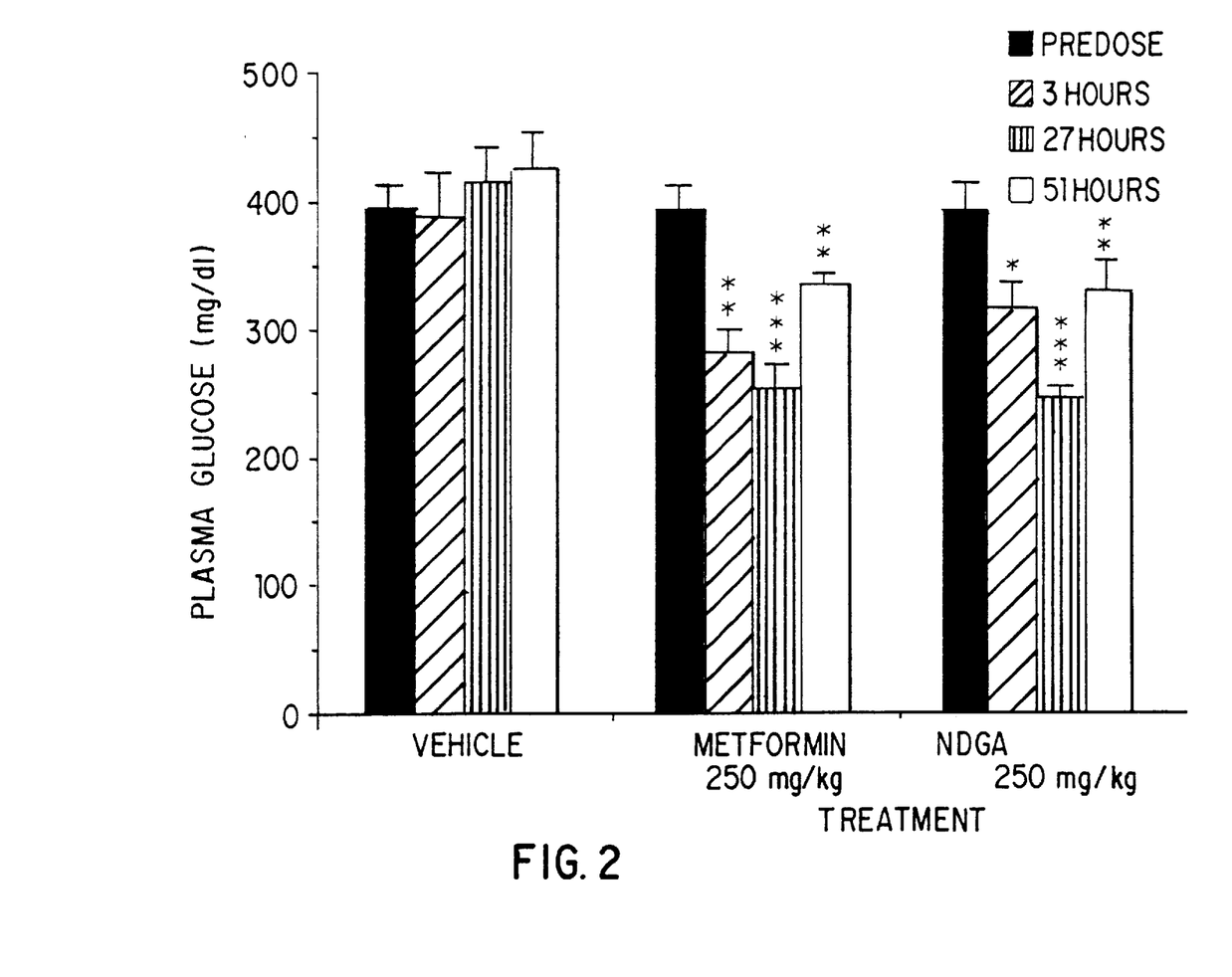
FIG. 2 is a histogram showing the plasma glucose levels of diabetic ob/ob mice treated either with a 250mg/kg dose of Metformin or with the same dose of NDGA. (*$P<0.05$, $P<0.01$, *$P<0.001$ (Anova)).

As shown in FIG. 2 and below in Table 3, oral administration of NGDA to diabetic C57BL/6J ob/ob mice once daily for 3 days at dosage levels of 250 mg/kg resulted in significant reduction of plasma glucose. Statistically significant glucose reduction relative to vehicle (control) was observed after 3 hours of each dose.

TABLE 3

Effects of NGDA on Blood Glucose in Diabetic ob/ob Mice

| Treatment | Dose (mg/kg) | Change in Glucose (mg/dL) 3 h | P Value | Change in Glucose (mg/dL) 27 h | P Value | Change in Glucose (mg/dL) 51 h | P Value |
|---|---|---|---|---|---|---|---|
| Vehicle | — | −8.4 | NA | 19.4 | NA | 29.9 | NA |
| Metformin | 250 q.d. | −113.4 | 0.0016 | −141.4 | <0.0001 | −60.6 | 0.0077 |
| NGDA | 250 q.d. | −78.3 | 0.0291 | −148.1 | <0.0001 | −63.6 | 0.0077 |

NA = nonapplicable

The change in body weight and overall food consumption values for mice administered with NGDA are shown in Table 4. A slight decrease of the body weight and food consumption were observed with NGDA treatment.

TABLE 4

Effects of NGDA on Body Weight and Food Consumption in Diabetic ob/ob Mice

| Treatment | Dose (mg/kg) | Change in Body Weight (g) 0–48 h | Food Consumption (g/mouse/24 h) 0–48 h |
|---|---|---|---|
| Vehicle | — | 0.3 | 4.9 |
| Metformin | 250 q.d. | −0.3 | 4.5 |
| NGDA | 250 q.d. | −0.6 | 3.7 |

Based on the above results, NGDA has a beneficial effect lowering plasma glucose in the ob/ob model.

6.3 BENEFICIAL EFFECT ON GLUCOSE DISPOSAL

This example illustrates the beneficial effects of NDGA on glucose disposal.

Protocol

Animals and experimental conditions were the same as described in Section 6.1, above. Diabetic mice designated C57BLIKS-db/db received orally by gavage daily for 2 days, either vehicle, NDGA administered at 150 mg/kg bid (9:00 and 17:00), 250 and 350 mg/kg q.d., or metformin [250 mg (1510 mol)/kg q.d]. Animals were fasted overnight prior to receiving the third day dose of the compounds. On day three of the study, an oral glucose load (2 g/kg) was given three hours -post-treatment. Blood was obtained from the tail vein prior to administration of the glucose load (t=0), and at 15, 30, 30, and 120 minutes following the glucose load, and analyzed for plasma glucose levels.

Results

Figure 3:
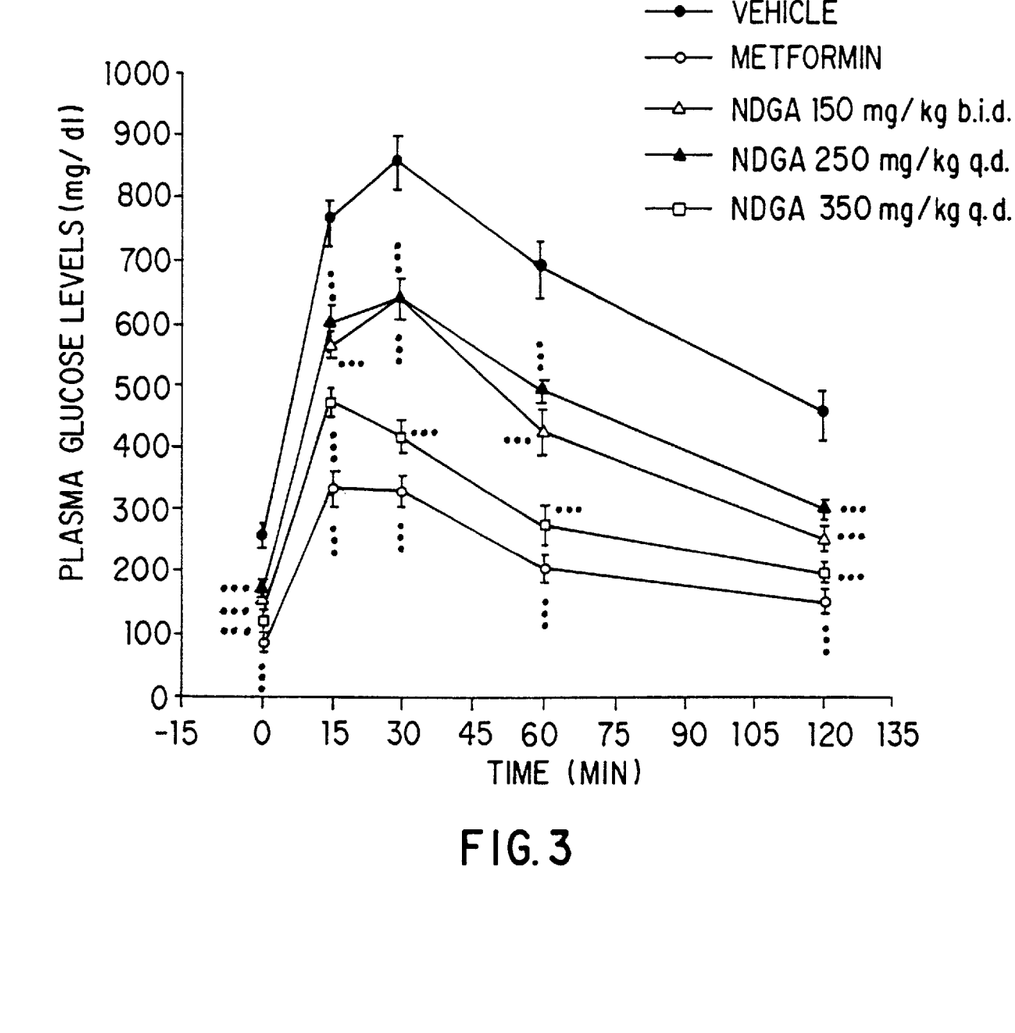
FIG. 3 shows the results of an oral glucose tolerance test for varying doses of NDGA. (***$P<0.0001$ (Anova, one factor)).
Figure 4:
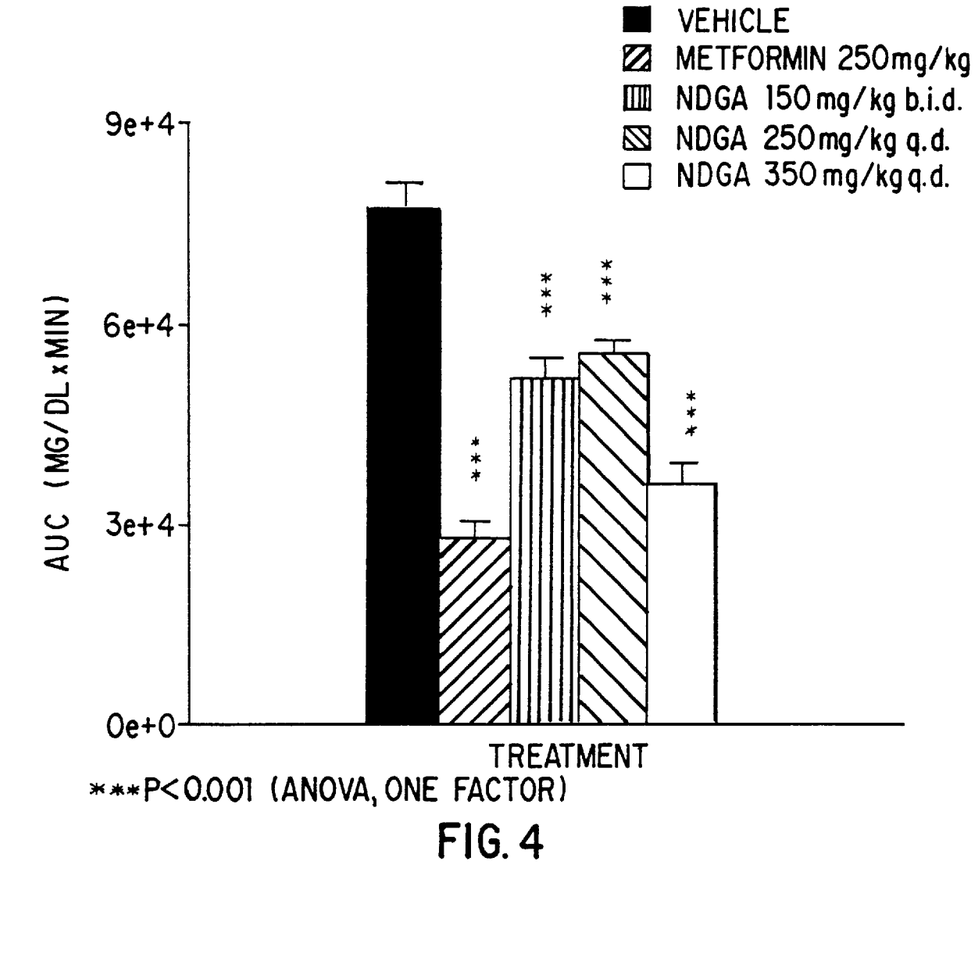
FIG. 4 shows the area under of the curve (AUC) for the oral glucose tolerance test of NDGA. (***$P<0.001$ (Anova, one factor)).

FIG. 3 and 4 show the effect of NDGA in the oral glucose tolerance test. NDGA at all dosage-levels significantly suppressed the postprandial glucose levels at all timepoints after the glucose load. The oral glucose tolerance was significantly improved as indicated by the area under the curve. This effect was dose dependent. These data indicate that NDGA enhances glucose utilization and improves the rate of glucose disposal in an animal model of insulin resistance, obesity, and NIDDM.

6.4 STIMULATION OF GLUCOSE TRANSPORT

This example illustrates the ability of NDGA to directly stimulate glucose transport in 3T3-L1 adipocytes, an art recognized in vitro system that represents an important mode of action for glucose utilization and disposal in mammals.

Protocol

Murine 3T3-L1 pre-adipocytes (American Type Culture Collection CL 173) were maintained in Dulbecco's modified Eagles medium (DMEM) containing 10% (v/v) supplemented calf serum, antibiotics, and 25 mM glucose. Cells were seeded in 24-well cluster plates (10,000 cells/well), grown to confluence (typically 5 days), and induced to differentiate 2 days postconfluence (day 0) according to the standard protocol of Frost and Lane (Frost, S. and Lane, M.D., 1985, *J. Biol. Chem.*, 260:2646–2652). Following differentiation, adipocytes were maintained in DMEM containing 10% fetal bovine serum, and provided with fresh medium every 2–3 days. Adipocytes employed in this study were used on days 7–10 postdifferentiation.

On the day of the experiment, adipocytes were washed with phosphate-buffered saline and switched to serum-free DMEM medium. Adipocytes were treated (in triplicate) for 18 hr with the indicated concentrations of NDGA. Concentrated stock solutions of NDGA were freshly prepared in dimethyl sulfoxide (DMSO) and diluted into culture medium. The final concentration of DMSO was 0.4% (v/v) which was also included in basal conditions. Following overnight (18 hr) treatment, the culture medium was aspirated and the monolayers washed with Krebs-Ringer Hepes buffer.

To assess the effects of the compounds on basal glucose transport, 2-deoxy-D-glucose uptake (an indicator of glucose transport) was measured in the absence of insulin stimulation. To determine if 18 hr exposure to compounds potentiated the stimulatory effect of insulin, adipocytes were further treated with 0.5 nM insulin (a sub-maximal concentration) for 30 minutes at 37° C. Under these assay conditions, 0.5 nM insulin stimulates glucose transport by approximately 200–400% over basal (typically 50 nmoles 2-deoxyglucose/ 10 minutes/well), and 100 nM insulin (a maximally effective concentration) stimulates glucose transport by approximately 1000–1500% over basal. Glucose transport assays were initiated by the addition of 2-deoxy-D-[$^3$H]glucose (0.5 $\mu$Ci/ml; 100 $\mu$M final concentrations) to each well followed by incubation for 10 min at 22° C. Assays were terminated by aspirating the media and rapidly washing the monolayer two times with ice-cold phosphate-buffered saline solution. Cell monolayers were solubilized in 0.1N NaOH, transferred to scintillation vials, and radioactivity determined by liquid scintillation counting. All data were corrected for non-specific hexose uptake determined in parallel samples treated for 5 minutes with 200 $\mu$M cytochalasin B.

Results

Figure 5:
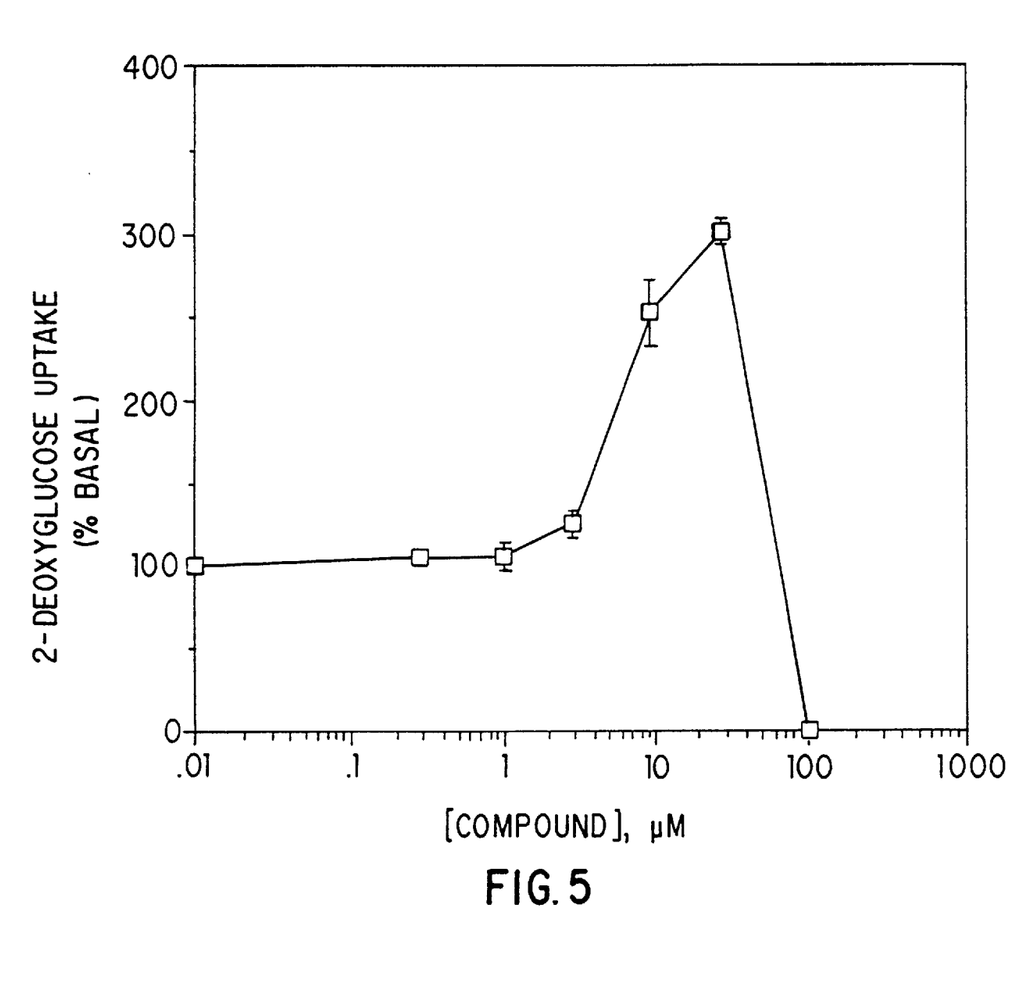
FIG. 5 shows the effect of NDGA on basal 2-deoxyglucose uptake in 3T3-L1 adipocytes.
Figure 6:
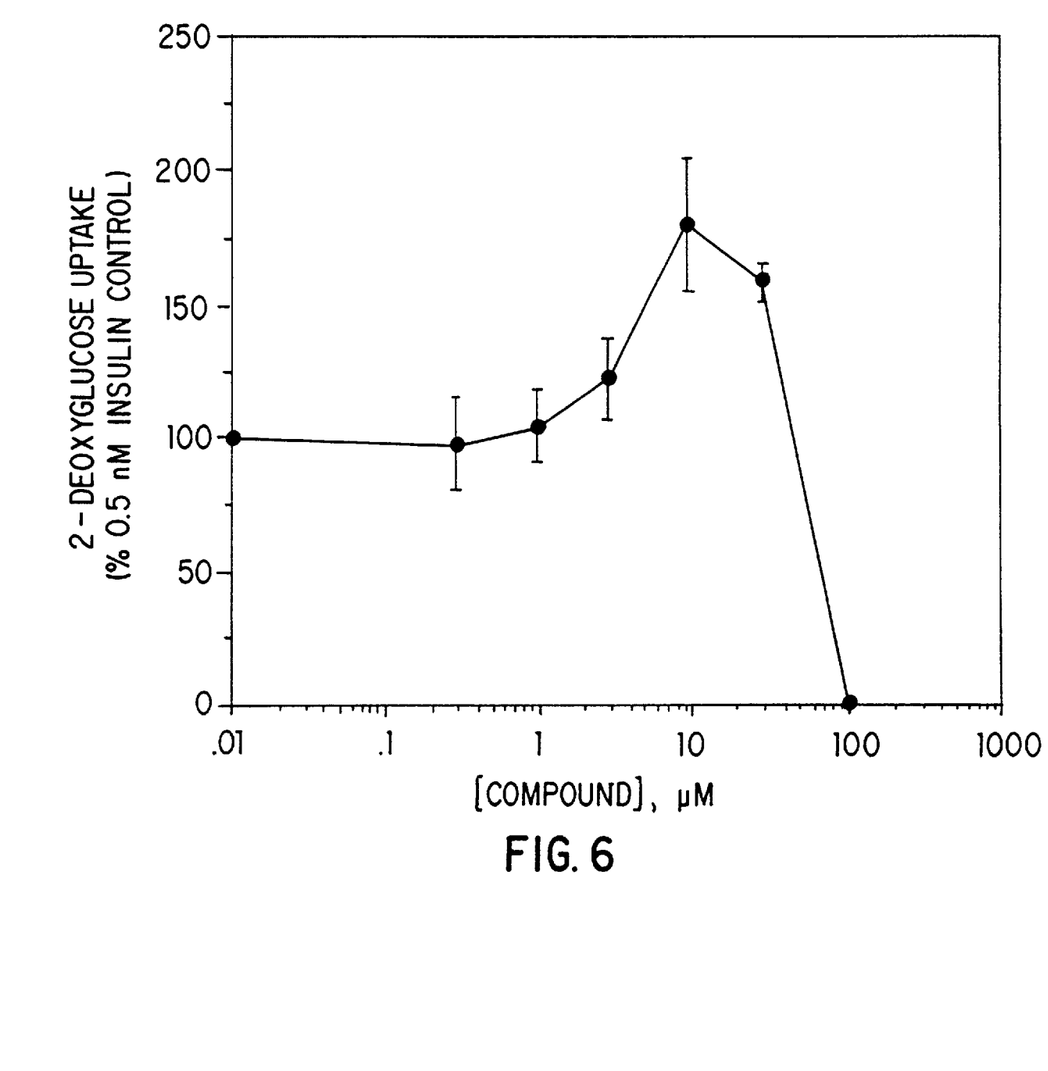
FIG. 6 shows the effect of NDGA on insulin-stimulated 2-deoxyglucose uptake in 3T3-L1 adipocytes.

NDGA increased the rate of basal glucose transport (i.e. no added insulin) in 3T3-L1 adipocytes by approximately 250% at 10 $\mu$M and by approximately 300% at 30 $\mu$M (FIG. 5). NDGA (10 and 30 $\mu$M) also sensitized the glucose transport system in adipocytes to subsequent stimulation with a sub-maximal concentration of insulin (0.5 nM). NDGA potentiated glucose transport in response to insulin by approximately 60% and 80% (FIG. 6). As would be recognized by those skilled in the art, these data indicate that the pure compound NDGA directly stimulates glucose transport in vitro, an effect that is consistent with the in vivo findings of enhanced glucose disposal and the ability to lower blood glucose.

What is claimed is:

1. A method for reducing blood glucose which comprises administering to a mammal a composition whose active ingredient consists essentially of nordihydroguaiaretic acid or a pharmaceutically acceptable salt thereof.

2. A method according to claim 1, wherein the compound is administered at a dose of 1–1000 mg per kg per day.

3. A method according to claim 1, wherein the compound is administered orally, parenterally, rectally or by inhalation.

* * * * *